United States Patent [19]
Jolesz et al.

[11] Patent Number: 5,752,515
[45] Date of Patent: May 19, 1998

[54] METHODS AND APPARATUS FOR IMAGE-GUIDED ULTRASOUND DELIVERY OF COMPOUNDS THROUGH THE BLOOD-BRAIN BARRIER

[75] Inventors: Ferenc A. Jolesz, Brookline; Kullervo Hynynen, Medfield, both of Mass.

[73] Assignee: Brigham & Women's Hospital, Boston, Mass.

[21] Appl. No.: 711,289

[22] Filed: Aug. 21, 1996

[51] Int. Cl.$^6$ .................................................. A61B 5/00
[52] U.S. Cl. ........................ 128/653.1; 128/653.2; 128/653.4; 128/654; 128/660.01; 604/22
[58] Field of Search ....................... 128/653.1, 653.2, 128/653.4, 654, 660.01, 898; 601/2, 3, 4; 424/9.3; 604/22, 890.1, 892.1

[56] References Cited

U.S. PATENT DOCUMENTS

| | | | |
|---|---|---|---|
| 3,499,437 | 3/1970 | Balamuth . | |
| 4,303,636 | 12/1981 | Gordon . | |
| 4,315,514 | 2/1982 | Drewes et al. . | |
| 4,923,437 | 5/1990 | Gordon .................................... | 600/12 |
| 5,059,415 | 10/1991 | Neuwelt . | |
| 5,112,596 | 5/1992 | Malfroy-Camine ................... | 424/2 |
| 5,291,890 | 3/1994 | Cline et al. ........................... | 128/653.2 |
| 5,307,816 | 5/1994 | Hashimoto et al. ................. | 128/660.03 |
| 5,368,032 | 11/1994 | Cline et al. ........................... | 128/653.2 |
| 5,438,989 | 8/1995 | Hochman et al. ................... | 128/653.1 |
| 5,443,068 | 8/1995 | Cline et al. ........................... | 128/653.5 |
| 5,465,718 | 11/1995 | Hochman et al. ................... | 128/653.1 |
| 5,485,839 | 1/1996 | Aida et al. ........................... | 128/653.1 |
| 5,524,620 | 6/1996 | Rosenschein ....................... | 128/653.1 |
| 5,526,814 | 6/1996 | Cline et al. ........................... | 128/653.2 |

OTHER PUBLICATIONS

Ryan et al, "Experimental Brain Hyperthermia: Techniques for Heat Delivery and Thermometry", *Int J. Radiation Oncology Biol. Phys.* vol. 20., pp. 739–750, 1991.

Le Bihan and Turner, "The Capillary Network: A Link between IVIM and Classical Perfusion", *Magnetic Resonance in Medicine* vol. 27, pp. 171–178, 1992.

Hills and James, "Microbubble Damage to the Blood–Brain Barrier: Relevance to Decompression Sickness", *Undersea Biomedical Research*, vol. 18, No. 2, pp. 111–116, 1991.

Polyashuk, "Permeability of Hemato–Encephasic Barrier Under the Effect of Supersonic Vibrations", *Permeability of Hemato–Encephalic Barrier*, p. 415 (parent abstract).

J.T. Patrick et al, "Focal Modification of the Blood–Brain Barrier with High Intensity Ultrasound: Experimental Results and Potential Application for Brain Tumor Therapy" *Clinical Research*, vol. 35, No. 1, 1987 (Parent abstract).

Mitragotri et al, "Ultrasound–Mediated Transdermal Protein Delivery" *Science* vol. 269, pp. 850–853, Aug. 11, 1993.

Vykhodtseva et al, "Histologic Effects of High Intensity Pulsed Ultrasound Exposure With Subharmonic Emission in Rabbit Brain In Vivo", *Ultrasound in Med. & Biol.* vol. 21, Not. 7, pp. 969–979, 1995.

J.T. Patrick et al, "Ultrasound and the Blood–Brain Barrier" In *Consensus on Hyperthermia for the 1990s*, Ed. H. I. Bicher et al, Plenum Press, New York 1990.

*Primary Examiner*—Marvin M. Lateef
*Assistant Examiner*—Shawna J. Shaw
*Attorney, Agent, or Firm*—Choate, Hall & Stewart

[57] ABSTRACT

Image-guide methods and apparatus for ultrasound delivery of compounds through the blood-brain barrier to selected locations in the brain target a selected location in the brain and applying ultrasound to effect in the tissues and/or fluids at that location a change detectable by imaging. At least a portion of the brain in the vicinity of the selected location is imaged, e.g., via magnetic resonance imaging, to confirm the location of that change. A compound, e.g., a neuropharmaceutical, in the patient's bloodstream is delivered to the confirmed location by applying ultrasound to effect opening of the blood-brain barrier at that location and, thereby, to induce uptake of the compound there.

59 Claims, 5 Drawing Sheets

METHODS AND APPARATUS FOR IMAGE-GUIDED ULTRASOUND DELIVERY OF COMPOUNDS THROUGH THE BLOOD-BRAIN BARRIER

BACKGROUND OF THE INVENTION

The invention pertains to medical systems and, more particularly, to methods and apparatus for delivery of compounds through the blood-brain barrier to the brain.

The blood-brain barrier prevents many compounds in the blood stream from entering the tissues and fluids of the brain. Nature provides this mechanism to insure a toxin-free environment for neurologic function. However, it also prevents delivery to the brain of compounds, such as neuropharmaceuticals, potential neuropharmaceuticals, and other neurologically active agents, that might otherwise remedy or modify neurologically-related activities and disorders.

Today, non-surgical treatments of neurologic disorders are limited to systemic introduction of compounds through the blood stream. A drawback of this form of treatment, as suggested above, is the relatively small number of known compounds that pass through the blood-brain barrier. Even those that do cross the barrier often produce adverse reactions in other parts of the body or in non-targeted regions of the brain.

Prior art surgical treatments of neurologic disorders are limited to removal or ablation of brain tissue. While these treatments have proven effective for certain localized disorders, such as tumors, they involve delicate, time-consuming procedures that may result in destruction of otherwise healthy tissues. The surgical treatments are generally not appropriate for disorders in which diseased tissue is integrated into healthy tissues, except in instances where destruction of the latter will not unduly effect neurologic function.

Patrick, et al, "Ultrasound and the Blood-Brain Barrier," *Consensus on Hyperthermia for the 1990's* (Plenum, 1990), pp. 369, et seq., suggest that focused ultrasound might be used to introduce chemotherapeutic agents through the barrier. The article is specifically directed to the use of ultrasound to modify the blood-brain barrier at targets within feline and canine brains and, thereby, to increase the barrier's permeability to a circulating dye/albumin complex. Ultrasound targeting, according to the article, is accomplished by surgically exposing the dura matter and positioning thereon a transducer/lens complex. Targets are located via stereotactic coordinates, as determined from directly-visualized or roentgenographically-visualized cranial structures. Delivery of ultrasound in the manner disclosed in the article resulted in histologically irreversible damage. Though the authors suggest that chemotherapeutic agents, such as monoclonal antibodies and immunotoxins, might also be introduced into the brain by ultrasonic modification of the blood-brain barrier, they state that further research would be necessary to determine whether permeability can be increased sufficiently for these high molecular weight compounds.

An object of this invention is to provide improved methods and apparatus for delivery of compounds to the brain, particularly, through the blood-brain barrier.

A further object of the invention is to provide such methods and apparatus as can be employed to deliver such compounds to precise locations within the brain.

A still further objects of the invention is to provide such methods and apparatus as can deliver compounds through the blood-brain barrier without surgery.

Yet another object of the invention is to provide such methods and apparatus as can deliver a full range of compounds through the blood-brain barrier.

Yet stiff another object of the invention is to provide cost-effective methods and apparatus for delivery of compounds through the blood-brain barrier.

Still further objects of the invention are to provide improved methods and apparatus for remedying or modifying neurological and neurologically-related activities and disorders via delivery of compounds through the blood-brain barrier.

SUMMARY OF THE INVENTION

These and other objects are attained by the invention which provides methods and apparatus for image-guided ultrasound delivery of compounds through the blood-brain barrier to selected locations in the brain.

A method according to one aspect of the invention includes targeting a selected location in the brain and applying ultrasound to induce, in the central nervous system (CNS) tissues and/or fluids at that location, a change detectable by imaging. At least a portion of the brain in the vicinity of the selected location is imaged, e.g., via magnetic resonance imaging, to confirm the location of the change. A compound, e.g., a neuropharmaceutical, in the patient's bloodstream is delivered to the confirmed location by applying ultrasound to effect opening of the blood-brain barrier at that location (or a location based thereon) and, thereby, to induce uptake of the compound there.

In one aspect of the invention, the change induced in the CNS tissues and/or fluids by ultrasound is heating or cavitation. The location of that change is confirmed by characteristic patterns in the image. In another aspect, the change is the uptake of contrast agents (or other compounds detectable by imaging) induced at the selected location via ultrasonic "opening" of the blood-brain barrier there. Again, the location of such change can be confirmed by characteristic patterns generated during imaging. In the text that follows, the change induced in the CNS tissues and/or fluids by ultrasound is referred to as "ultrasonically-induced change," "imaging-detectable change," and similar such terms).

In a further aspect, the invention provides methods that combine the above-described targeting and delivery steps in order to introduce a compound through the blood-brain barrier. The invention of this aspect calls for delivering a compound from the patient's bloodstream to a selected location in the brain by applying ultrasound to that location. Delivery to the selected location is confirmed by imaging the brain to confirm ultrasonically-induced change there. Particularly, where the compound is itself can be detected via imaging, confirmation is made by imaging the brain during or after delivery, and by identifying the compund's characteristic pattern at the selected location. Where the compound itself cannot be detected by imaging, confirmation is made by imaging the brain during delivery, and by identifying in the image patterns representative of ultrasonically-induced heating or ultrasonically-induced cavitation at the desired location.

In a further aspect, the invention provides methods as described above in which ultrasound is applied to the selected location in the patient's brain by surgically exposing the dura matter and by applying ultrasound through the exposed dura matter.

In a preferred aspect, the ultrasound is applied through the skull itself, e.g., via a phased array of transducers, a focused ultrasound transducer, or the combination of an ultrasound source (e.g., transducer) and an acoustic lens, placed outside the skull. According to this aspect of the invention, there is no need to perform a craniectomy or other surgical procedure on the patient.

The invention provides, in still further aspects, methods as described above in which the brain is imaged via magnetic resonance imaging, positron emission tomography, or computed tomography in order to confirm ultrasonically-induced change at the selected location in the brain.

According to further aspects of the invention, such change is ultrasonically induced in the brain at the selected location by cavitation and, particularly, by applying ultrasound to the selected location of the brain at frequencies ranging from 20 kHz to 5 MHz, and with sonication duration ranging from 100 nanoseconds to 1 minute.

In a related aspect of the invention, delivery of compounds through the blood-brain barrier is induced at the selected location by cavitation and, particularly, by applying ultrasound to the selected location of the brain at frequencies ranging from 20 kHz to 10 MHz, sonication duration ranging from 100 nanoseconds to 30 minutes, with continuous wave or burst mode operation, where the burst mode repetition varies from 0.01 Hz to 1 MHz.

Likewise, according to further aspects of the invention, imaging-detectable change is ultrasonically induced in the brain at the selected location by heating and, particularly, by applying ultrasound to the selected location of the brain at frequencies ranging from 200 kHz to 10 MHz, and with sonication duration ranging from 100 milliseconds to 30 minutes.

In a related aspect of the invention, delivery of compounds through the blood-brain barrier is induced at the selected location by heating and, particularly, by applying ultrasound to the selected location of the brain at frequencies ranging from 250 kHz to 10 MHz, and with sonication duration ranging from 0.10 microseconds to 30 minutes.

Other aspects of the invention provide methods as described above in which ultrasound is applied to the selected location in the brain at a focal region sized in accord with the volume of CNS tissue and/or fluids to which the compound is to be delivered. That region can range from 1 $mm^3$–1 $cm^3$.

Still further aspects of the invention provide methods as described above for image-guided ultrasonic delivery of compounds through the blood-brain barrier, where the compounds administered into the patient's bloodstream include, by way of non-limiting example, any of neuropharmacologic agents, neuroactive peptides (e.g., hormones, gastrointestinal peptides, angiotensin, sleep peptides, etc.), proteins (e.g. calcium binding proteins), enzymes (e.g., cholineacetyltransferase, glutamic acid decarboxylase, etc.), gene therapy agents, neuroprotective or growth factors, biogenic amines (e.g., dopamine, GABA), trophic factors to brain or spinal transplants, immunoreactive proteins (e.g, antibodies to neurons, myelin, antireceptor antibodies), receptor binding proteins (e.g., opiate receptors), radioactive agents (e.g., radioactive isotopes), antibodies, and cytotoxins, among others.

Related aspects of the invention provide methods for treating neurological disorders by image-guided ultrasonic delivery of compounds through the blood-brain barrier in accord with the methods described above. Such disorders include tumors, cancer, degenerative disorders, sensory and motor abnormalities, seizure, infection, immunologic disorder, mental disorder, behavioral disorder, and localized CNS disease, among others.

In still further related aspects, the invention provides methods for modification of neurologic and neurologically-related activity (e.g., behavioral activity, memory-related activity, and sexual activity, among others) by such methods.

The invention provides, in still further aspects, an apparatus for image-guided ultrasonic delivery of compounds through the blood-brain barrier.

Such an apparatus, according to one aspect of the invention, includes an ultrasound source and a targeting mechanism for applying ultrasound generated thereby to a selected location of the brain to effect change a change there that is detectable by imaging. An imaging element generates a radiologic image of at least a portion of the brain in the vicinity of the selected location and, thereby, permits confirmation of that location. The apparatus further includes a delivery mechanism for applying ultrasound to the confirmed location (or a location based thereon) to effect opening of the blood-brain barrier at that location and, thus, to induce delivery there of a compound from the bloodstream.

By way of further example, an apparatus according to further aspects of the invention utilizes as an ultrasound source, a phased array, a focused ultrasound transducer, or the combination of an ultrasound source and an acoustic lens, capable of applying ultrasound to the targeted location through the skull itself, without need for surgery to expose the brain.

Still other aspects of the invention provide an apparatus as described above incorporating functionality for effecting the methods described above.

These and other aspects of the invention are evident in the drawings and in the description that follows.

BRIEF DESCRIPTION OF THE DRAWINGS

A more complete understanding of the invention may be attained by reference to the drawings in which.

DETAILED DESCRIPTION OF THE ILLUSTRATED EMBODIMENT

Figure 1:
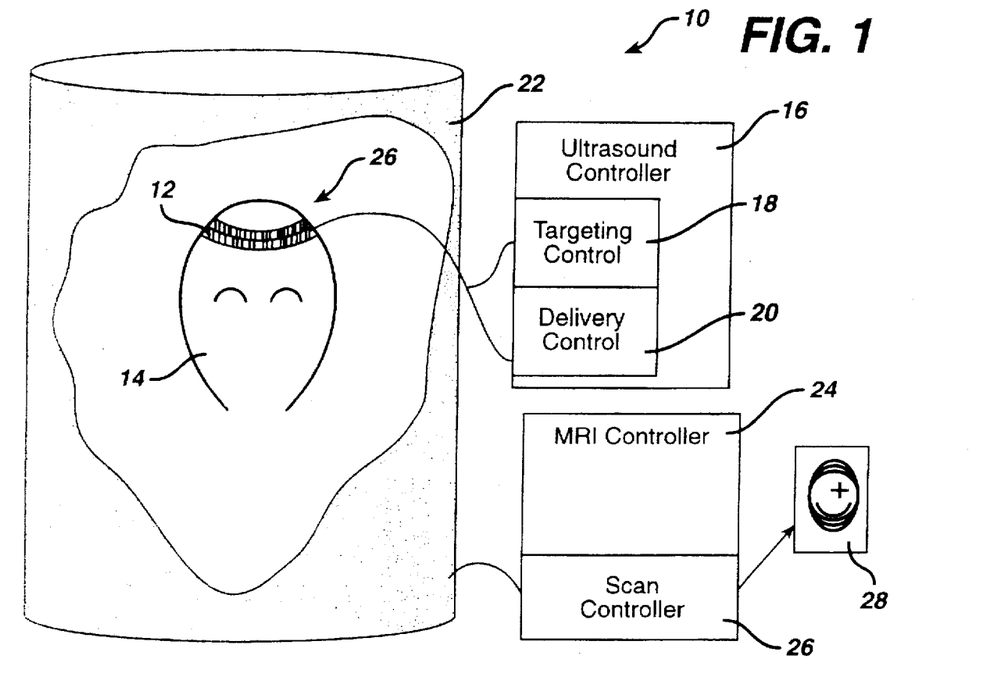
FIG. 1 depicts an apparatus according to the invention for image-guided ultrasonic delivery of compounds through the blood-brain barrier.

FIG. 1 depicts an apparatus 10 according to the invention for image-guided ultrasonic delivery of compounds through the blood-brain barrier. The apparatus 10 includes an ultrasound source, shown here as a phased array of transducers 12 disposed about the head 14 of a human patient. The phased array 12 is powered and controlled by ultrasound controller 16, which includes targeting control element 18 that tunes and drives array 12 to apply ultrasound to a selected location in the patient's brain so as to effect there a change (e.g., heating, cavitation or uptake of contrast agent) that is detectable by imaging. The controller 16 also includes delivery control element 20 that tunes and drives array 12 to apply ultrasound to open the blood-brain barrier at that same location and, thereby, to induce delivery a compound from the patient's bloodstream to the brain at that location.

The apparatus 10 further includes a magnetic resonance imaging (MRI) device, comprising magnetic gradient coil and radiofrequency coil 22 and MRI controller 24, together capable of generating an image of at least a portion the patient's head (and, more particularly, of the patient's brain) to permit confirmation of ultrasonically induced change at the selected location. Controller 24 comprises scanning control functionality 26 for generating an magnetic resonance image 28 of the patient's head 14. A headholder (not shown) holds the patient's head 14 in place within the MRI tube 22, as shown.

The phased array 12 applies focused ultrasound to selected locations within the patient's brain. The array 12 can be constructed in the manner of the aperiodic ultrasound phased array disclosed in United States Provisional Patent Application No. 60/006,413, filed Nov. 9, 1995, for APERIODIC ULTRASOUND PHASED ARRAY, assigned to the assignee hereof, the teachings of which are incorporated herein by reference.

Phased array 12 is operated in accord with the teachings herein to deliver ultrasound, through the patient's skull, in doses suitable for inducing non-destructive imaging-detectable change (e.g., heating, cavitation or uptake of contrast agent) and/or non-destructive opening of the blood-brain barrier at selected locations within the brain.

In alternate embodiments, a focused ultrasound transducer, or the combination of an ultrasound source and an acoustic lens, is substituted for the phased array 12 as a means of generating ultrasound and applying it to the brain. In such alternate embodiments, the focused ultrasound transducer, or source/lens combination, is mechanically moved in order to target differing locations within the brain (as opposed to the phased array which is aimed "electronically"). The design of such transducers and acoustic lens, is well known in the art.

More particularly, under control of targeting control 18, phased array 12 delivers ultrasound to a selected location in the brain to heat or to cause cavitation in the tissues, fluids and other structures there sufficient to induce imaging-detectable change at that location, i.e., change in the CNS tissues and/or fluids that can be detected in images generated by the illustrated imaging device. That change may constitute direct heating or cavitation of the tissues and/or fluids or, alternatively, it may constitute the uptake of contrast agent induced by opening the blood-brain barrier at the selected location. The direct inducement of imaging-detectable change is discussed immediately below. Inducement via the uptake of contrast agent is discussed later, in connection with FIG. 4.

In a preferred embodiment of the invention for use with human patients, direct non-destructive heat-based imaging-detectable change is induced at the selected location in the brain applying ultrasound to the selected location of the brain at frequencies ranging from 200 kHz to 10 MHz, and with sonication duration ranging from 100 milliseconds to 30 minutes.

Likewise, direct non-destructive cavitation-based imaging-detectable change is induced at the selected location in the brain applying ultrasound to the selected location of the brain at frequencies ranging from 20 kHz to 5 MHz, and with sonication duration ranging from 100 nanoseconds to 1 minute. In contrast to imaging-detectable changes induced by heating, those induced by cavitation occur at higher peak intensity levels within this range.

Likewise, under control of delivery control 18, phased array 12 delivers ultrasound to the selected location in the brain (or a location based thereon) to heat or to cause cavitation sufficient to open the blood-brain barrier, thereby, effecting uptake of neuropharmaceuticals, potential neuropharmaceuticals or other compounds in the blood into that location of the brain.

In a preferred embodiment of the invention for use with human patients, non-destructive heat-based opening of the blood-brain barrier is induced at the selected location in the brain applying ultrasound to the selected location of the brain at frequencies ranging from 250 kHz to 10 MHz, and with sonication duration ranging from 0.10 microseconds to 30 minutes.

Likewise, non-destructive cavitation-based opening of the blood-brain barrier is induced at the selected location in the brain applying ultrasound to the selected location of the brain at frequencies ranging from 20 kHz to 10 MHz, sonication duration ranging from 100 nanoseconds to 30 minutes, with continuous wave or burst mode operation, where the burst mode repetition varies from 0.01 Hz to 1 MHz.

A further appreciation of the ultrasound dosing levels for opening the blood-brain barrier may be attained by reference to Vykhodtseva et al., "Histologic Effects of High Intensity Pulsed Ultrasound Exposure with Subharmonic Emission in Rabbit Brain In Vivo", *Ultrasound in Medicine and Biology*, vol. 21, 1995, pp. 969–979 and, particularly, to teachings therein with respect to the effect of differing ultrasound pulse intensities on blood-brain barrier permeability. That article, and those teachings in particular, are incorporated herein by reference.

The magnetic resonance imaging device, including MRI device 22 and MRI controller 24, comprises a conventional, commercially available MRI device. The device is operated in the conventional manner known in the art in order to generate images 28 of the patient's head (and, particularly, of the brain) in accord with the teachings herein.

It will be appreciated that any device permitting determination of the location of change in the CNS tissues and/or fluids effected by the phased array 12 (e.g., under control of targeting control 18) in the patient's brain may be substituted for the magnetic resonance imaging device. Preferably, however, the substituted device is itself a radiologic imaging device, such as, by way of non-limiting example, a computed tomography (CT) imaging device, positron emission tomography (PET) imaging device. In further embodiments of the invention, other medical imaging devices capable of detecting, distinguishing and/or locating tissues, fluids, masses, structures, substances, conditions, and other features (naturally occurring or otherwise) within the human body and, particularly, within the head and brain, are used in place of MRI, CT or PET imaging devices. These other medical imaging devices include, by way of non-limiting example, ultrasound imaging devices, X-ray imaging devices, and gamma camera imaging devices, among others.

To this end, as used herein the terms "image," "radiologic image," and the like, refer to results (whether or not human readable) generated by MRI, CT or PET imaging devices, or by such other imaging devices for use in detecting, distinguishing and/or locating tissues, fluids, masses, structures, substances, conditions, and other features (naturally occurring or otherwise) within the human body and, particularly, within the head and brain. Likewise, the terms "radiologically imaging," "imaging" and the like refer to the act of obtaining such results.

Figure 2:
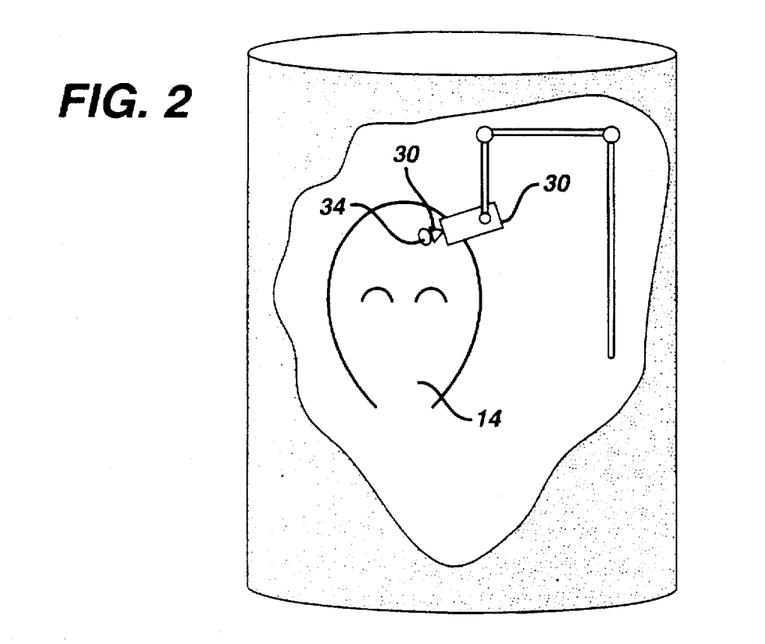
FIG. 2 depicts an alternative configuration for an ultrasound source used in practice of the invention.

FIG. 2 depicts an alternative configuration for an ultrasound source used in practice of the invention. The source comprises an ultrasound transducer 30 in combination with a lens 30. As above, this arrangement permits focused doses of ultrasound to be applied to target's within the patient's 14 brain for inducing non-destructive imaging-detectable changes and/or non-destructive opening of the blood-brain barrier at selected locations within the brain. The illustrated source is applied directly to the dura matter, following surgical removal of corresponding portions of the scalp and skull (as illustrated by hole 34). As above, the source is powered and controlled by an ultrasound controller 16, not illustrated.

In a preferred embodiment, an ultrasound source is used to deliver ultrasound doses through the skull, obviating the need for surgery. The source is fabricated from piezoelectric material that converts an electrical signal applied on the electrode surfaces of the material to mechanical motion of the applicator. The piezoelectric material has a backing of low (for example air) or high acoustic impedance to maximize energy output through the front surface of the applicator. The electrical signal for each transducer element is provided by a signal generator and amplified by a radio frequency (RF) amplifier. The ultrasound energy can be focused by making the piezoelectric element curved or inserting a lens in front of the applicator. In these cases a minimum of one transducer is required. By using multiple transducers enhanced focusing effect may be produced.

In the case of a phased array a number of piezoelectric elements are operating together with each of them having their own RF amplifier. The electrical signals for each element are provided by a phase shifter that introduces a proper phase shift between the driving signals so that the ultrasound waves launched by each element form a common focus at a desired locations. This phase shift is modified such that the effect of skull bone and other intervening tissues between the element and the target point is compensated for so that all of the waves come to a common focus regardless of their propagation medium. The effect of the skull and other tissues are calculated based on image information (for example CT or MRI) on its properties. Thus, the phased arrays allow elimination of phase shifts introduced by skull bone that destroys an ultrasound beam focus of a focused beam at frequencies above about 1 MHz. In addition, the phased arrays can eliminate a movement in the focal location caused by the skull during a lower frequency sonication.

Figure 3:
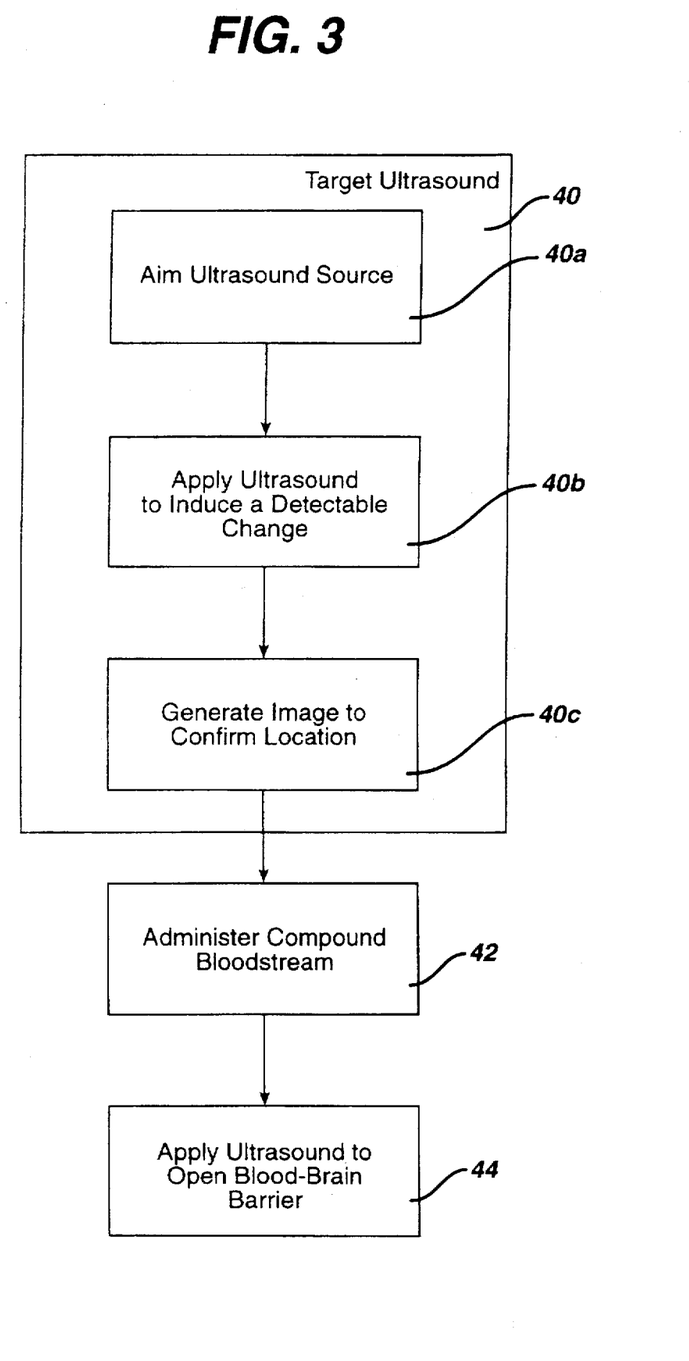
FIG. 3 depicts a method according to the invention for image-guided ultrasonic delivery of compounds through the blood-brain barrier.

FIG. 3 depicts a method of operating the apparatus 10 of FIG. 1 in order to effect image-guided ultrasonic delivery of compounds through the blood-brain barrier. In step 40, the ultrasound source is aimed to target the selected location within the patient's brain. Particularly, in sub-step 40a, the ultrasound source is aimed at the selected location. In sub-step 40b, the ultrasound source is activated to apply a dose sufficient to directly effect imaging-detectable change in the CNS tissues and/or fluids at the selected location as described above.

In sub-step 40c, at least a portion of the brain in the vicinity of the selected location is imaged, e.g., via the imaging device shown in FIG. 1, to confirm the location of the imaging-detectable change. Confirmation is made, via a human or an automated image reader, via identification of patterns characteristic of ultrasonically-induced heating or cavitation at expected locations in the image. In instances where the patterns do not appear at the expected location, sub-steps 40a–40c are repeated with revised aiming of the ultrasound source.

In instances where the ultrasound applied in step 40b effects temporary changes in CNS function (e.g., a taste sensation, a tingling sensation, an involuntary muscle motion or cessation thereof, etc.), detection of those functional changes can also be used to confirm the selected location targeted in sub-step 40a.

Once aiming of the ultrasound source has been confirmed in step 40, the compound intended for delivery through the blood-brain barrier is administered into the patient's bloodstream, e.g., via injection, ingestion, inhalation, or other such method. In the case of injection, the compound can be administered in the vicinity of the brain, e.g., via injection into the carotid artery.

These compounds can include, by way of non-limiting example, neuropharmacologic agents, neuroactive peptides (e.g., hormones, gastrointestinal peptides, angiotensin, sleep peptides, etc.), proteins (e.g. calcium binding proteins), enzymes (e.g., cholineacetyltransferase, glutamic acid decarboxylase, etc.), gene therapy, neuroprotective or growth factors, biogenic amines (e.g., dopamine, GABA), trophic factors to brain or spinal transplants, immunoreactive proteins (e.g, antibodies to neurons, myelin, antireceptor antibodies), receptor binding proteins (e.g., opiate receptors), radioactive agents (e.g., radioactive isotopes), antibodies, and cytotoxins, among others.

In addition, compounds to be administered into the bloodstream in step 40 can include high molecular weight complexes formed by combining relatively inert substances, such as EDTA, with neuropharmaceuticals or other substances currently known to pass through the blood-brain barrier. Due to their sizes and/or molecular configurations, such complexes are prevented from crossing the barrier, except at selected locations in the brain opened via ultrasound as described herein. Use of such complexes in connection with the invention, therefore, permits localized application of compounds that might otherwise produce unwanted effects in other parts of the brain or body.

In step 42, the compound(s) are delivered from the blood stream to the selected (and confirmed) location in the patient's brain by application of an ultrasound that effects opening of the blood-brain barrier at that location and, thereby, to induces uptake of the compound there. Ultrasound doses necessary to achieve this are discussed above.

It will be appreciated that administration of the compound in step 42 need not necessarily precede application of the ultrasound in step 44. Because the ultrasonically-opened blood-brain barrier typically permits uptake of administered compounds for at least a short period of time, the compound 42 can be introduced into the blood stream after the barrier-opening ultrasound dose is applied.

As an alternative to applying ultrasound and delivering compounds to the confirmed location, an embodiment of the invention calls for taking at least one of these actions with respect to a location based on the confirmed location. Thus, for example, neurophysiological properties or constraints may necessitate delivering the compound (and, therefore, applying the barrier-opening ultrasound) to a location different from—but based on—that location targeted in step 40.

Figure 4:
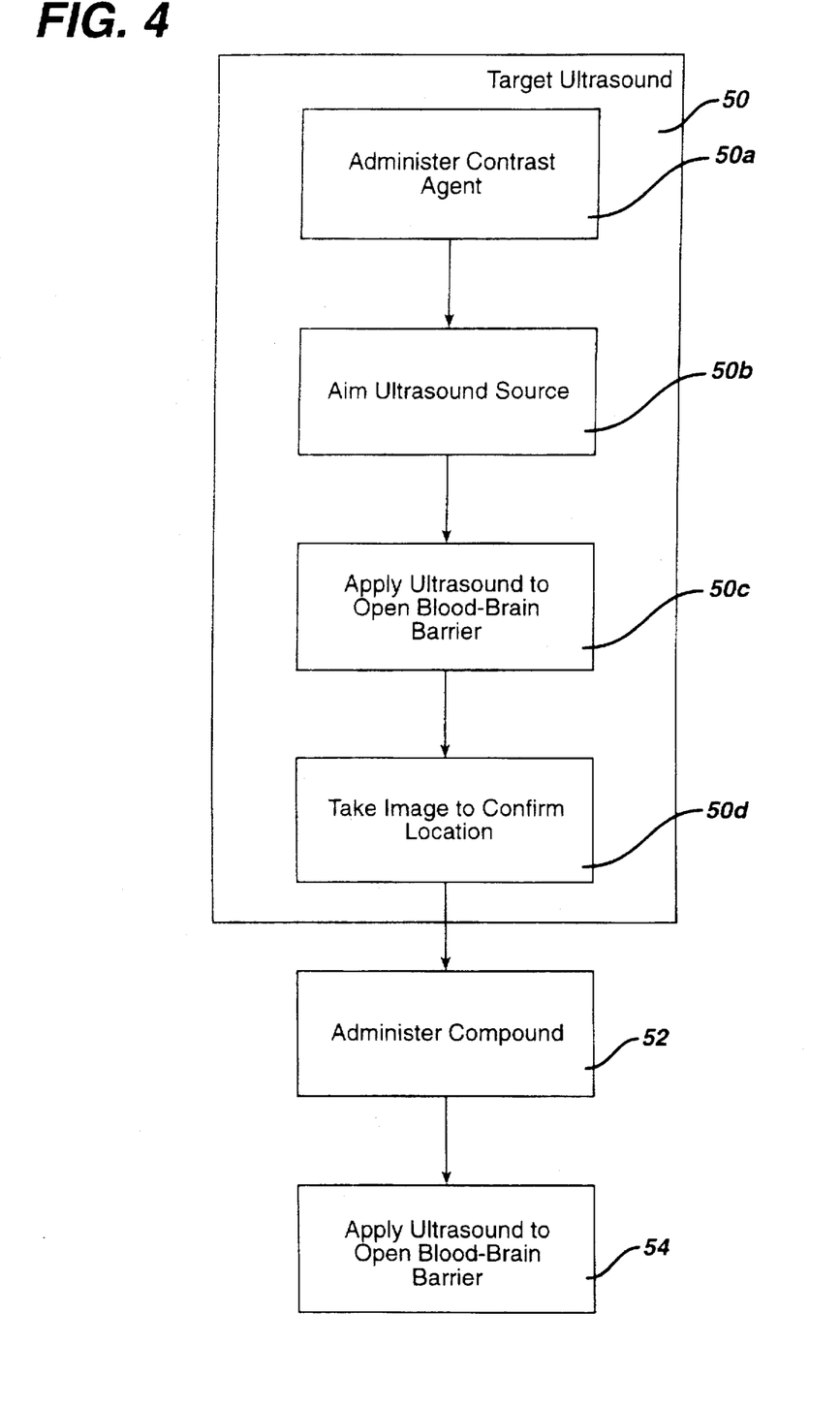
FIG. 4 depicts an alternative method according to the invention for image-guided ultrasonic delivery of compounds through the blood-brain barrier.

FIG. 4 depicts an alternative method of operating the apparatus 10 of FIG. 1 to effect image-guided ultrasonic delivery of compounds through the blood-brain barrier. In step 50, the ultrasound source is aimed to target the selected location within the patient's brain. Particularly, in sub-step 50a, a contrast agent is introduced into the patient's bloodstream, e.g., via injection, ingestion, inhalation, or other such method. In sub-step 50b, the ultrasound source is aimed to dose a selected location in the brain. In sub-step 50c, the ultrasound source is activated to apply a dose sufficient to open the blood-brain barrier at the selected location and, thereby, induce uptake of the contrast agent there.

As above, it will be appreciated that administration of the compound in sub-step 50a need not necessarily precede application of the ultrasound in sub-step 50c due to the period during which the blood-brain barrier typically remains open.

In sub-step 50d, at least a portion of the brain in the vicinity of the selected location is imaged, e.g., via the imaging device shown in FIG. 1, to confirm the location of the imaging-detectable change—to wit, the uptake of a contrast agent at the selected location. Confirmation is made, via a human or an automated image reader, via identification of patterns characteristic of the contrast agent at expected locations in the image. In instances where the patterns do not appear at the expected location, sub-steps 50a–50d with revised aiming of the ultrasound source.

As above, in instances where the compound induced for uptake in sub-step 50c effects temporary changes in CNS function (e.g., a taste sensation, a tingling sensation, an involuntary muscle motion or cessation thereof, etc.), this can also be used to confirm the selected location targeted in sub-step 40a. To this end, the compound introduced in step 50a can be selected so as to induce such temporary changes in CNS function.

Once aiming of the ultrasound source has been confirmed, step 52 of the method calls for administration into the patient's bloodstream of the compound intended for delivery. This proceeds in the manner of step 42, described above. Further, in step 54, those compound(s) are delivered from the blood stream to the selected (and confirmed) location in the patient's brain. This proceeds in the manner of step 44, described above.

As above, an alternative to applying ultrasound and delivering compounds to the confirmed location, an embodiment of the invention calls for taking at least one of these actions with respect to a location based on the confirmed location. Thus, for example, neurophysiological properties or constraints may necessitate delivering the compound (and, therefore, applying the barrier-opening ultrasound) to a location different from—but based on—that location targeted in step 50.

Figure 5:
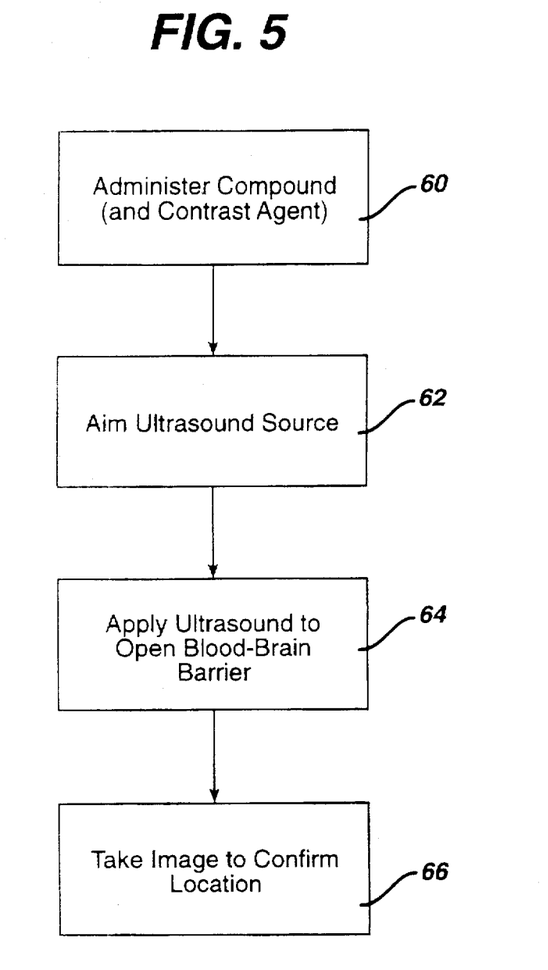
FIG. 5 depicts another alternative method according to the invention for image-guided ultrasonic delivery of compounds through the blood-brain barrier.

FIG. 5 depicts another alternative method of operating the apparatus 10 of FIG. 1 to effect image-guided ultrasonic delivery of compounds through the blood-brain barrier. In step 60, the compound intended for delivery through the blood-brain barrier is administered into the patient's bloodstream. Optionally, a contrast agent is also be administered to the bloodstream at this time. As above, these compounds can be administered via injection, ingestion, inhalation, or other such methods.

In step 62, the ultrasound source is aimed to dose a selected location in the brain. In step 64, the ultrasound source is activated to apply a dose sufficient to open the blood-brain barrier at the selected location and, thereby, induce uptake of the compound and optional contrast agent there. As above, it will be appreciated that administration of the compound in step 60 need not necessarily precede application of the ultrasound in step 64 due to the period during which the blood-brain barrier typically remains open.

In step 66, at least a portion of the brain in the vicinity of the selected location is imaged, e.g., via the imaging device shown in FIG. 1, to confirm the location of the ultrasound dosing. If no contrast agent was administered in step 60, confirmation is made by identifying patterns characteristic of ultrasonically-induced cavitation or heating in the image. In these instances, step 66 is preferably performed concurrently with step 64. If a contrast agent was administered in step 60, confirmation is made by identification of patterns characteristic of the contrast agent at expected locations in the image. In these instances, step 66 is preferably performed subsequent to step 64.

In instances where the compound induced for uptake in sub-step 64 effects temporary changes in CNS function (e.g., a taste sensation, a tingling sensation, an involuntary muscle motion or cessation thereof, etc.), this can also be used to confirm the selected location targeted in step 62.

The methods and apparatus described in the embodiments above can be employed for treating neurological disorders by image-guided ultrasonic deliver of compounds through the blood-brain barrier. Such disorders include tumors, cancer, degenerative disorders, sensory and motor abnormalities, seizure, infection, immunologic disorder, mental disorder, behavioral disorder, and localized CNS disease, among others. For example, as an alternative to conventional functional neurosurgery, the foregoing apparatus and methods can be used to introduce selective cytotoxins into selected locations of the brain to destroy all or selected cell types there. Likewise, these apparatus and methods can be employed to introduce immunologic agents at those selected locations. Still further, they can be employed in neural pathway tracing studies using retrograde or anteretrograde axonal transport, or in neurophysiological testing using localized delivery of activation or inhibition.

In still further related aspects, the invention provides methods for modification of neurologic and neurologically-related activity (e.g., behavioral activity, memory-related activity, and sexual activity, among others) by such methods.

Described above are methods and apparatus for image-guided ultrasound delivery of compounds through the blood-brain barrier meeting the above-cited goals. It will be appreciated that the embodiments described herein are illustrative and that other embodiment, incorporating modifications, fall within the scope of the invention.

Figure 6A:
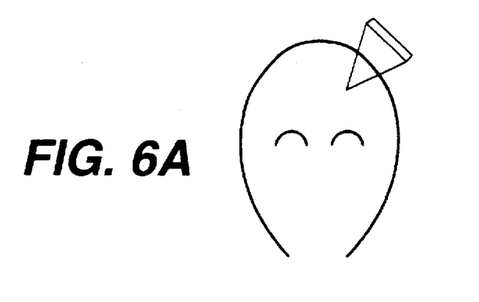
FIGS. 6A–G depict configurations of ultrasound sources and lenses used in practice of the invention.
Figure 6B:
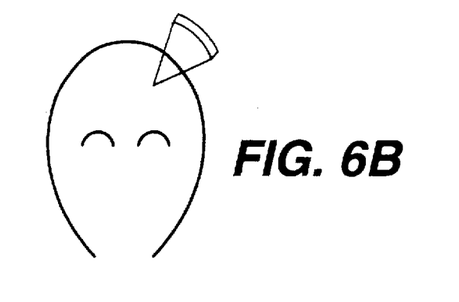
Figure 6C:
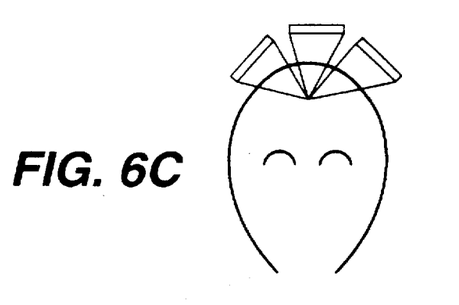
Figure 6D:
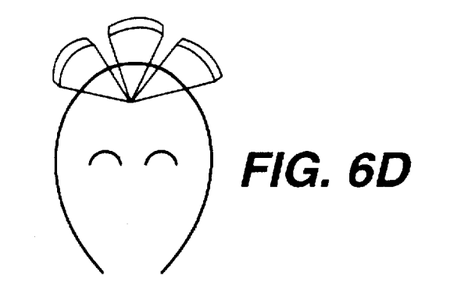
Figure 6E:
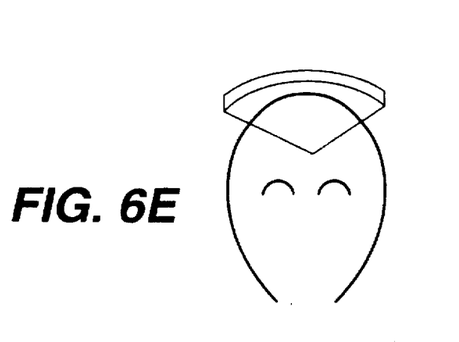
Figure 6F:
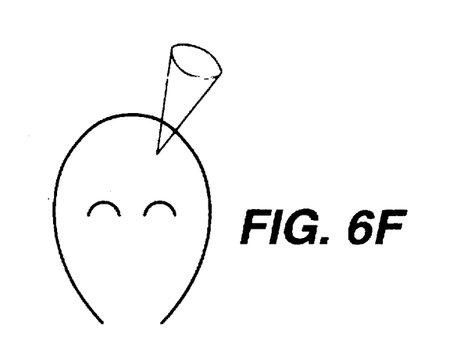
Figure 6G:
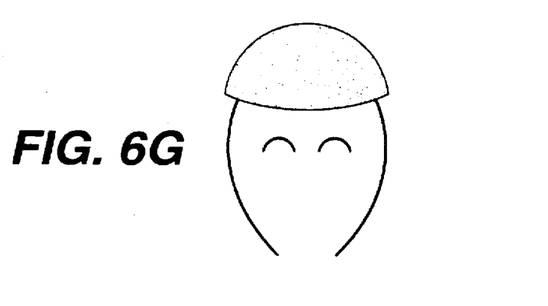

For example, a variety of ultrasound sources may be used to practice the invention. Such sources are shown, by way of non-limiting example, in FIGS. 6A–6F. Thus, FIGS. 6A–6B illustrate the use of a single linear and curvilinear phased array as ultrasound sources. Likewise, FIGS. 6C–6D illustrate the use of a multiple linear and curvilinear phased arrays as ultrasound sources. FIG. 6E illustrates the use of a large lens to focus an ultrasound beam generated by a source (not shown). FIG. 6F illustrates the use of a smaller lens to focus such a beam. Finally, FIG. 6G illustrates the use of a partially spherical phased array as an ultrasound source. As above, the beams generated by these sources may pass through the skull or through the exposed dura matter.

In view thereof, what we claim is:

1. A method for delivering a compound from the bloodstream to a selected location in the brain, the method comprising:

A. applying ultrasound to a selected location in the brain to effect at that location a change detectable by imaging, B. generating a radiologic image of at least a portion in the brain to confirm the location of that change, and C. applying ultrasound to the confirmed location in the brain, or a location based thereon, to open the blood-brain barrier at that location and, thereby, induce uptake at that location a compound from the bloodstream.

2. A method according to claim 1, wherein steps (A) and (C) include the step of delivering the ultrasound through the skull.

3. A method according to claim 2, wherein steps (A) and (C) include the step of delivering the ultrasound using any of (i) a phased array, (ii) a focused ultrasound transducer, and (iii) a combination of an ultrasound source and acoustic lens.

4. A method according to claim 1, wherein steps (A) and (C) include the steps of
exposing dura matter of the brain,
delivering the ultrasound substantially at or beneath the exposed dura matter.

5. A method according to claim 1, wherein step (B) includes the step of generating a radiologic image of at least a portion of the brain in the vicinity of the selected location.

6. A method according to claim 1, comprising admitting the compound into the patient's bloodstream at least in a vicinity of the selected location.

7. A method according to claim 1, wherein step (C) includes the step of delivering the ultrasound to the confirmed location in the brain to open the blood-brain barrier by cavitation.

8. A method according to claim 7, wherein step (C) includes the step of delivering the ultrasound to the confirmed location in the brain at a frequency ranging from 20 kHz to 10 MHz, sonication duration ranging from 100 nanoseconds to 30 minutes, with continuous wave or burst mode operation, where the burst mode repetition varies from 0.01 Hz to 1 MHz.

9. A method according to claim 1, wherein step (C) includes the step of delivering the ultrasound to the confined location in the brain to open the blood-brain barrier by heating.

10. A method according to claim 9, wherein step (C) includes the step of delivering the ultrasound to the confirmed location in the brain at a frequency ranging from 250 kHz to 10 MHz, and with sonication duration ranging from 0.10 microseconds to 30 minutes.

11. A method according to claim 1, wherein step (A) includes the step of delivering the ultrasound to the selected location in the brain to induce by cavitation the change detectable by imaging.

12. A method according to claim 11, wherein step (A) includes the step of delivering the ultrasound to the selected location in the brain at a frequency ranging from 20 kHz to 5 MHz, and with sonication duration ranging from 100 nanoseconds to 1 minute.

13. A method according to claim 1, wherein step (A) includes the step of delivering the ultrasound to the selected location in the brain to induce by heating the change detectable by imaging.

14. A method according to claim 13, wherein step (A) includes the step of delivering the ultrasound to the selected location in the brain at a frequency ranging from 200 kHz to 10 MHz, and with sonication duration ranging from 100 milliseconds to 30 minutes.

15. A method according to any of claims 11–14, wherein step (A) includes the steps of
introducing a contrast agent into the patient, at least in a vicinity of the selected location in the brain, and
effecting a change at that location detectable by imaging by applying ultrasound there to open the blood-brain barrier and, thereby, induce uptake of the contrast agent there.

16. A method according to claim 1, wherein step (C) includes the step of introducing into the patient's bloodstream a compound including any of a contrast agent, a neuropharmacologic agent, a neuroactive peptides, a protein, an enzyme, a gene therapy agent, a neuroprotective factor, a growth factor, a biogenic amine, a trophic factor to any of brain and spinal transplants, an immunoreactive proteins, a receptor binding protein, a radioactive agent, an antibody, and a cytotoxin.

17. A method for delivering a compound to a selected location in the brain of a patient, the method comprising:

A. introducing a contrast agent into the patient's bloodstream, at least in a vicinity of the selected location in the brain, B. applying ultrasound to the selected location to open the blood-brain barrier and, thereby, induce uptake of the contrast agent there, C. taking a radiologic image of at least a portion of the brain to confirm the location to which ultrasound was delivered, D. introducing the compound into the patient's bloodstream at least in a vicinity of the confirmed location, and E. applying ultrasound to the confirmed location in the brain, or a location based thereon, to open the blood-brain barrier at that location and, thereby, induce uptake of the compound there.

18. An apparatus for delivering a compound to a selected location in the brain of a patient, the apparatus comprising:

A. an ultrasound source,

B. targeting means, coupled to the ultrasound source, for applying ultrasound to the selected location in the brain to effect at that location a change detectable by imaging, C. imaging means for generating a radiologic image of at least a portion of the brain to confirm the location of that change, and D. delivery means, coupled to the ultrasound source, for applying ultrasound to the confirmed location in the brain, or a location based thereon, to open the blood-brain barrier at that location and, thereby, induce uptake of the compound there.

19. An apparatus according to claim 18, wherein at least one of the targeting means and the delivery means includes means for delivering the ultrasound through the skull.

20. An apparatus according to claim 19, wherein at least one of the targeting means and the delivery means comprises any of (i) a phased array, (ii) a focused ultrasound transducer, and (iii) a combination of an ultrasound source and acoustic lens.

21. An apparatus according to claim 18, wherein at least one of the targeting means and the delivery means includes means for delivering the ultrasound substantially at or beneath exposed dura matter.

22. An apparatus according to claim 18, wherein the imaging means comprises means for generating a radiologic image of at least a portion of the brain in the vicinity of the selected location.

23. An apparatus according to claim 18, wherein the delivery means includes means for delivering the ultrasound to the confirmed location in the brain to open the blood-brain barrier by cavitation.

24. An apparatus according to claim 23, wherein the delivery means includes means for delivering the ultrasound to the confirmed location in the brain at a frequency ranging from 20 kHz to 10 MHz, sonication duration ranging from 100 nanoseconds to 30 minutes, with continuous wave or burst mode operation, where the burst mode repetition varies from 0.01 Hz to 1 MHz.

25. An apparatus according to claim 18, wherein the delivery means includes means for delivering the ultrasound to the confirmed location in the brain to open the blood-brain barrier by heating.

26. An apparatus according to claim 25, wherein the delivery means includes means for delivering the ultrasound to the confirmed location in the brain at a frequency ranging from 250 kHz to 10 MHz, and with sonication duration ranging from 0.10 microseconds to 30 minutes.

27. An apparatus according to claim 18, wherein the targeting means includes means for delivering the ultrasound to the selected location in the brain to effect radiologic activity by cavitation.

28. An apparatus according to claim 27, wherein the targeting means includes means for delivering the ultrasound to the selected location in the brain at a frequency ranging from 20 kHz to 5 MHz, and with sonication duration ranging from 100 nanoseconds to 1 minute.

29. An apparatus according to claim 18, wherein the targeting means includes means for delivering the ultrasound to the selected location in the brain to induce by heating the change detectable by imaging.

30. An apparatus according to claim 29, wherein the targeting means includes means for delivering the ultrasound to the selected location in the brain at a frequency ranging from 200 kHz to 10 MHz, and with sonication duration ranging from 100 milliseconds to 30 minutes.

31. An apparatus for delivering a compound to a selected location in the brain of a patient, the method comprising,
   A. an ultrasound source,
   B. targeting means, coupled to the ultrasound source, for applying ultrasound to the selected location to open the blood-brain barrier and, thereby, induce uptake of the contrast agent there,
   C. imaging means for taking a radiologic image of at least a portion of the brain to confirm the location to which ultrasound was delivered, and
   D. delivery means, coupled to the ultrasound source, for applying ultrasound to the confirmed location in the brain, or a location based thereon, to open the blood-brain barrier at that location and, thereby, induce uptake of the compound there.

32. A method for delivering a compound from the bloodstream to a selected location in the brain, the method comprising:
   A. applying ultrasound to a selected location in the brain to (i) induce a change at that location detectable by imaging, and (ii) open the blood-brain barrier at that location and, thereby, induce uptake of the compound at that location, and
   B. generating a radiologic image of at least a portion in the brain to confirm the location of the change detectable by imaging.

33. A method according to claim 32, wherein step (A) includes the step of delivering the ultrasound through the skull.

34. A method according to claim 33, wherein step (A) includes the step of delivering the ultrasound using any of (i) a phased array, (ii) a focused ultrasound transducer, and (iii) a combination of an ultrasound source and acoustic lens.

35. A method according to claim 32, wherein step (A) includes the steps of
   exposing dura matter of the brain,
   delivering the ultrasound substantially at or beneath the exposed dura matter.

36. A method according to claim 32, wherein step (B) includes the step of generating a radiologic image of at least a portion of the brain in the vicinity of the selected location.

37. A method according to claim 32, comprising admitting the compound into the patient's bloodstream at least in a vicinity of the selected location.

38. A method according to claim 32, wherein step (A) includes the step of delivering the ultrasound to the selected location in the brain to induce at that location a change detectable by imaging and to open the blood-brain barrier by cavitation.

39. A method according to claim 38, wherein step (A) includes the step of delivering the ultrasound to the selected location in the brain at a frequency ranging from 20 kHz to 10 MHz, sonication duration ranging from 100 nanoseconds to 30 minutes, with continuous wave or burst mode operation, where the burst mode repetition varies from 0.01 Hz to 1 MHz.

40. A method according to claim 32, wherein step (A) includes the step of delivering the ultrasound to the selected location in the brain to induce by heating the change detectable by imaging and to open the blood-brain barrier.

41. A method according to claim 40, wherein step (A) includes the step of delivering the ultrasound to the selected location in the brain at a frequency ranging from 250 kHz to 10 MHz, and with sonication duration ranging from 0.10 microseconds to 30 minutes.

42. A method according to claim 32, wherein step (A) includes the step of introducing into the patient's bloodstream a compound including any of a contrast agent, a neuropharmacologic agent, a neuroactive peptides, a protein, an enzyme, a gene therapy agent, a neuroprotective factor, a growth factor, a biogenic amine, a trophic factor to any of brain and spinal transplants, an immunoreactive proteins, a receptor binding protein, a radioactive agent, an antibody, and a cytotoxin.

43. An apparatus for delivering a compound to a selected location in the brain of a patient, the apparatus comprising:
   A. an ultrasound source,
   B. targeting/delivery means, coupled to the ultrasound source, for applying ultrasound to the selected location in the brain to (i) effect a change at that location detectable by imaging, and (ii) open the blood-brain barrier at that location and, thereby, induce uptake of the compound there, and
   C. imaging means for generating a radiologic image of at least a portion of the brain to confirm the location of the change detectable by imaging.

44. An apparatus according to claim 43, wherein targeting/delivery means includes means for delivering the ultrasound through the skull.

45. An apparatus according to claim 44, wherein targeting/delivery means comprises any of a (i) a phased array, (ii) a focused ultrasound transducer, and (iii) a combination of an ultrasound source and acoustic lens.

46. An apparatus according to claim 43, wherein targeting/delivery means includes means for delivering the ultrasound substantially at or beneath exposed dura matter.

47. An apparat us according to claim 43, wherein the imaging means comprises means for generating a radiologic image of at least a portion of the brain in the vicinity of the selected location.

48. An apparatus according to claim 43, wherein the targeting/delivery means includes means for delivering the ultrasound to the selected location in the brain to induce by cavitation a change detectable by imaging and to open the blood-brain barrier.

49. An apparatus according to claim 48, wherein the targeting/delivery means includes means for delivering the ultrasound to the confirmed location in the brain at a frequency ranging from 20 kHz to 10 MHz, sonication duration ranging from 10 nanoseconds to 30 minutes, with continuous wave or burst mode operation, where the burst mode repetition varies from 0.01 Hz to 1 MHz.

50. An apparatus according to claim 43, wherein the targeting/delivery means includes means for delivering the ultrasound to the confirmed location in the brain to induce by heating the change detectable by imaging and to open the blood-brain barrier by heating.

51. An apparatus according to claim 50, wherein the targeting/delivery means includes means for delivering the ultrasound to the confirmed location in the brain at a frequency ranging from 250 kHz to 10 MHz, and with sonication duration ranging from 0.10 microseconds to 30 minutes.

52. A method for delivering a compound from the bloodstream to a selected location in the brain of a patient, the method comprising:
   A. applying ultrasound to a selected location in the brain to effect at that location a change detectable by imaging,
   B. generating a radiologic image of at least a portion in the brain to confirm the location of that change,
   C. further confirming that location by a change in central nervous system function of the patient,
   D. applying ultrasound to the confirmed location in the brain, or a location based thereon, to open the blood-brain barrier at that location and, thereby, induce uptake of the compound at that location.

53. A method for delivering a compound from the bloodstream to a selected location in the brain of a patient, the method comprising:
   A. applying ultrasound to a selected location in the brain to effect a change in a central nervous system function of the patient,
   B. confirming that location by a change in that central nervous system function, and
   C. applying ultrasound to the confirmed location in the brain, or a location based thereon, to open the blood-brain barrier at that location and, thereby, induce uptake of the compound at that location.

54. A method for delivering a compound from the bloodstream to a selected location in the brain, the method comprising:
   A. applying ultrasound to a selected location in the brain to (i) induce a change at that location detectable by imaging, and (ii) open the blood-brain barrier at that location and, thereby, induce uptake of the compound at that location,
   B. generating a radiologic image of at least a portion in the brain to confirm the location of the change detectable by imaging, and
   C. further confirming that location by a change in central nervous system function of the patient.

55. A method for delivering a compound from the bloodstream to a selected location in the brain of a patient, the method comprising:
   A. applying ultrasound to a selected location in the brain to (i) a change in a central nervous system function of the patient, and (ii) open the blood-brain barrier at that location and, thereby, induce uptake of the compound at that location, and
   B. confirming that location by detecting a change in that central nervous system function.

56. A method for treating at least one of a neurological and a neurologically-related disorder, the method comprising:
   A. applying ultrasound to a selected location in the brain to effect at that location a change detectable by imaging,
   B. generating a radiologic image of at least a portion in the brain to confirm the location of that change,
   C. applying ultrasound to the confirmed location in the brain, or a location based thereon, to open the blood-brain barrier at that location and, thereby, induce uptake at that location of a compound in the bloodstream.

57. A method for treating at least one of a neurological and a neurologically-related disorder, the method comprising:
   A. applying ultrasound to a selected location in the brain to effect at that location a change detectable by imaging,
   B. generating a radiologic image of at least a portion in the brain to confirm the location of that change,
   C. applying ultrasound to the confirmed location in the brain, or a location based thereon, to open the blood-brain barrier at that location and, thereby, induce uptake at that location of a compound in the bloodstream.

58. A method for modification of neurologic and neurologically-related activity, the method comprising:
   A. applying ultrasound to a selected location in the brain to effect at that location a change detectable by imaging,
   B. generating a radiologic image of at least a portion in the brain to confirm the location of that change,
   C. applying ultrasound to the confirmed location in the brain, or a location based thereon, to open the blood-brain barrier at that location and, thereby, induce uptake at that location of a compound in the bloodstream.

59. A method for functional neurosurgery, the method comprising:
   A. applying ultrasound to a selected location in the brain to effect at that location a change detectable by imaging,
   B. generating a radiologic image of at least a portion in the brain to confirm the location of that change,
   C. applying ultrasound to the confirmed location in the brain, or a location based thereon, to open the blood-brain barrier at that location and, thereby, induce uptake at that location of at least a selective cytotoxin in the bloodstream.

* * * * *